United States Patent [19]

Dolhyj et al.

[11] 4,219,687
[45] Aug. 26, 1980

[54] HYDROALKYLATION OF BENZENE AND ANALOGS

[75] Inventors: Serge R. Dolhyj, Parma; Louis J. Velenyi, Lyndhurst, both of Ohio

[73] Assignee: Standard Oil Company, Cleveland, Ohio

[21] Appl. No.: 928,220

[22] Filed: Jul. 26, 1978

[51] Int. Cl.² .................. C07C 5/10; C07C 15/12; C10G 23/02
[52] U.S. Cl. ..................... 585/267; 208/89; 208/144; 252/455 Z; 585/25; 585/268; 585/323; 585/427
[58] Field of Search ............. 260/668 R, 667, 668 D; 252/455 Z; 208/89, 144; 585/25, 323, 268, 425, 320, 427, 267

[56] References Cited

U.S. PATENT DOCUMENTS

| | | | |
|---|---|---|---|
| 3,784,617 | 1/1974 | Suggitt et al. | 260/668 R |
| 3,829,517 | 8/1974 | Zuech | 260/668 R |
| 3,839,477 | 10/1974 | Suggitt et al. | 260/668 R |
| 3,864,421 | 2/1975 | Suggitt | 260/668 R |
| 3,869,523 | 3/1975 | Suggitt et al. | 260/668 R |
| 4,093,671 | 6/1978 | Murtha et al. | 260/668 B X |
| 4,094,918 | 6/1978 | Murtha et al. | 260/668 B X |
| 4,094,920 | 6/1978 | Murtha et al. | 260/668 B X |
| 4,118,434 | 10/1978 | Murtha et al. | 260/668 B X |
| 4,122,125 | 10/1978 | Murtha et al. | 260/668 B X |

*Primary Examiner*—Delbert E. Gantz
*Assistant Examiner*—G. E. Schmitkons
*Attorney, Agent, or Firm*—Gary R. Plotecher; Herbert D. Knudsen; Larry W. Evans

[57] ABSTRACT

Mononuclear aromatic hydrocarbons, e.g. benzene and analogs, are converted by hydroalkylation to the corresponding cycloalkyl aromatics by contacting the mononuclear aromatic hydrocarbons in the presence of hydrogen with a catalyst comprising a rare earth-exchanged Y-type zeolite support carrying a promoter comprising at least one of ruthenium, iridium, rhodium and palladium, the catalyst being calcined in an oxygen-containing atmosphere at a temperature of 250° to 600° C. prior to the hydroalkylation reaction.

15 Claims, No Drawings

HYDROALKYLATION OF BENZENE AND ANALOGS

BACKGROUND OF THE INVENTION

The present invention relates to an improved process for the hydroalkylation of mononuclear aromatic hydrocarbons, namely benzene and analogs thereof, to form cycloalkylaromatics. Many patents have recently issued in the field of hydroalkylation of mononuclear aromatics. See, for example, U.S. Pat. No. 3,760,019, U.S. Pat. No. 3,784,617, U.S. Pat. No. 3,784,618, U.S. Pat. No. 3,829,514, U.S. Pat. No. 3,829,515, U.S. Pat. No. 3,829,516 and U.S. Pat. No. 3,829,517. In the processes disclosed in these patents, benzene or analog is contacted with a catalyst which is normally composed of a Group VIII transition metal supported on a suitable carrier, the catalyst optionally containing tungsten. Many different supports are disclosed as useful including silica-alumina, zeolite and alumina. Specific Group VIII transition metals disclosed to be useful are cobalt, nickel, ruthenium, rhodium, palladium, iridium and platinum.

Although processes disclosed in the foregoing patents are capable of effecting hydroalkylation of benzene and analogs to the corresponding cycloalkylaromatic compounds, they are disadvantageous in that they are unable to provide the desired cycloalkylaromatic product compounds with high yields and high selectivities. Moreover, in many processes it is necessary to subject the catalyst to be used to an activation pre-treatment by reducing the catalyst with $H_2$ prior to beginning the hydroalkylation reaction. In still other processes, it is necessary to carry out the hydroalkylation reaction in stages, the total amount of hydrogen necessary to effect hydroalkylation being added to the reaction system in stepped additions.

Accordingly, it is an object of the present invention to provide an improved process for the catalytic hydroalkylation of benzene and analogs to the corresponding cycloalkylaromatic compounds which produces the desired product compounds in higher yield and with higher selectivities than processes known prior to the present invention.

It is a further object of the present invention to provide a hydroalkylation process of the type described above which can be carried out either in batch mode or continuously in a single stage operation, i.e. a process which does not require stepped addition of reactants.

It is still another object of the present invention to provide a hydroalkylation process in which the catalyst to be used can be employed directly after calcination, $H_2$ reduction of the catalyst prior to use being unnecessary.

SUMMARY OF THE INVENTION

These and other objects are accomplished by the present invention in accordance with which mononuclear aromatic hydrocarbons are converted into cycloaklyl aromatics by contacting the mononuclear aromatic hydrocarbons in the presence of hydrogen with a catalyst comprising a rare earth-exchanged Y-type zeolite support carrying a promoter comprising at least one of ruthenium, iridium, rhodium and palladium.

More specifically, the present invention provides a process for the hydroalkylation of mononuclear aromatic hydrocarbons in which the mononuclear aromatic hydrocarbon together with hydrogen is contacted with a catalyst comprising a rare earth-exchanged Y-type zeolite support carrying a ruthenium, iridium, rhodium and/or palladium promoter, the catalyst being calcined in an oxygen-containing atmosphere at a temperature of 250° to 600° C. prior to the hydroalkylation reaction.

In a specific embodiment, the present invention provides a process for the hydroalkylation of mononuclear aromatic hydrocarbons which comprises contacting for a period of 10 minutes to 6 hours at a temperature of from room temperature to 400° C. hydrogen and a mononuclear aromatic hydrocarbon selected from the group consisting of benzene and substituted benzene substituted with 1 to 4 alkyl groups each independently having 1 to 4 carbon atoms with a catalyst obtained by calcining in a molecular oxygen-containing atmosphere at a temperature of about 250° to 600° C. a composite comprising a rare earth-exchanged Y-type zeolite support impregnated with at least one compound decomposable to yield a promoter comprising at least one of ruthenium, iridium, rhodium and palladium, the amount of the decomposable compound on the support being such that the amount of promoter on the support after calcination is between about 0.2 and 10 weight percent with the weight of the rare earth-exchanged Y-type zeolite plus the weight of the promoter being taken as 100%.

In accordance with the present invention it has been found that cycloalkylaromatics can be produced with higher yields and higher selectivities than previously known processes for hydroalkylation of benzene and analogs. For example, it has been found that cyclohexylbenzene can be obtained with per pass conversions approaching 50% at selectivities close to 80%, which is significantly better than obtainable with the prior art processes disclosed in the above-noted patents. Moreover, the inventive process can be accomplished in a single stage operation, i.e., without the stepped addition of reactants and hence is easier to carry out than conventional processes carried out in multiple stages. Also, the catalyst employed in the inventive process can be used directly after calcination without $H_2$ reduction, and hence practice of the inventive process is easier than conventional processes requiring $H_2$ reduction as part of the catalyst preparation.

DETAILED DESCRIPTION

Process Conditions

The inventive hydroalkylation reaction is accomplished by contacting the mononuclear aromatic hydrocarbon to be reacted with a reaction catalyst in the presence of hydrogen. The reaction can be accomplished both in batch mode and continuously with both fixed and fluid catalyst beds. The reaction is normally carried out in single stage operation, i.e., all of the reactants and the catalyst necessary for the reaction are brought together at the same time and not in stepped additions. However, the reaction can be carried out in stages if desired.

The reaction temperature is normally maintained between room temperature and 400° C., preferably 100° to 300° C., more preferably 150° to 250° C. and optionally 200° C. The reaction pressure is normally maintained at 100 to 800 psig, preferably 200 to 500 psig and most preferably 300 to 400 psig. When the reaction is carried out in the batch mode, the reactants and catalysts are contacted with one another for a period of 10 minutes to 6 hours, preferably more than ½ to 3 hours, and optionally about 1.5 hours. A reaction time of less than 10 minutes or more than 6 hours can be used if desired although better results will be obtained if the reaction time is maintained within this range. When the process is carried out on a continuous basis, the reactant/catalyst contact time is normally 10 seconds to 10 minutes, preferably 100 seconds to 5 minutes.

The amount of hydrogen in the reaction system is not critical, and the reaction will proceed so long as any amount of hydrogen is present. Preferably the amount of hydrogen corresponds to the amount of hydrogen present when a 600 cc reactor containing 5 grams of catalyst and 2.0 moles of benzene is filled with hydrogen to the pressures indicated above. If desired, a carrier gas which is inert to th e reactants, product and catalyst can be included in the reaction system.

The present invention finds wide applicability in the hydroalkylation of all types of mononuclear aromatic hydrocarbons. Benzene (unsubstituted) and substituted benzene substituted with 1 to 4 alkyl groups each independently having 1 to 4 carbon atoms can be readily converted to the corresponding cycloalkylaromatics in accordance with the present invention. Specific examples of compounds which can be processed by the present invention include benzene, ethylbenzene, cumene (isopropyl benzene), toluene, xylene, and durene (tetramethylbenzene).

In order to recover the product compound from the reaction mixture when the reaction is completed, the liquid reaction product is separated from any unreacted hydrogen and carrier gas that may be present in the system. The liquid reaction product is then filtered to remove catalysts therefrom and the filtrate is subjected to distillation or other suitable separation technique to recover the product compound from unreacted starting material.

CATALYST

The catalyst employed in the inventive process comprises a rare earth-exchanged Y-type zeolite impregnated with a small but suitable amount of a Group VIII transition metal promoter selected from the group consisting of ruthenium, iridium, rhodium and palladium. Y-type zeolite is a well-known material in the art and described in detail in Chapters 18-20 of Meier and Uytterhoeven, MOLECULAR SEIVES, American Chemical Society, Washington, D.C., copyright 1973. See also U.S. Pat. No. 3,130,007. As well-known in the art, Y-type zeolite can be treated to accept various types of ions by impregnating the Y-type zeolite with a solution of the ions to be accepted. Such a procedure causes an exchange reaction to occur, cations in the aqueous solution being exchanged for cations originally in the zeolite. See column 18 of U.S. Pat. No. 3,130,007. The catalyst support useful in the inventive process is a rare earth-exchanged Y-type zeolite which is produced by exchanging rare earth ions from an aqueous solution thereof with the ions originally in Y-type zeolite. This material is well-known as pointed out in columns 7 and 8 of U.S. Pat. No. 3,784,617. In the preferred embodiment of the invention, the rare earth-exchanged Y-type zeolite employed in Linde's SK-500, which is a well-known commercially available catalyst support. Linde's SK-500 is composed of 65.0 weight percent $SiO_2$, 22.7 weight percent $Al_2O_3$, 1.6 weight percent $Na_2O$ and 10.7 weight percent various rare earth metals. Rare earth-exchanged Y-type zeolites other than Linde's SK-500 can be employed in the present invention, the specific rare earth impregnating the Y-type zeolite being unimportant. In this connection, since it is expensive to separate one rare earth from another, commercially available rare earth-exchanged Y-type zeolites are made with mixtures of different rare earths rather than a single rare earth.

In accordance with the present invention, the rare earth-exchanged Y-type zeolite employed as the catalyst additionally contains a promoter metal selected from the group consisting of ruthenium, iridium, rhodium and palladium. The preferred promoter is ruthenium. The amount of promoter metal in the catalyst can vary between relatively broad proportions. If the amount of promoter metal is about 0.1 weight percent, no significant promoting effect will be obtained. Moreover, although amounts of promoter metal above 10% will provide effective catalysts, the cost of using such large amounts of promoter metal is prohibitively expensive. Therefore, the amount of promoter metal in the catalyst is greater than 0.1 weight percent and usually between 0.2 and 10 weight percent based on the weight of promoter metal in the catalyst with the weight of the rare earth-exchanged Y-type zeolite plus the weight of the promoter metal being taken as 100 percent. Preferably the catalyst contains 0.5 to 2 weight percent promoter metal, while the most preferred amount is about one percent by weight.

The ruthenium, iridium, rhodium and/or platinum promoted rare earth exchanged Y-type zeolite employed as the catalyst may additionally contain promoter metals selected from the group consisting of uranium, thorium, lanthanum, lanthanides, Group VIIB, Group IA elements and Group IB elements. Preferred catalysts contain ruthenium, copper and ruthenium, or copper, iridium and ruthenium. The amount of these additional promoter metals in the catalyst can be about 0.01 to 2 weight percent based on the total weight of the catalyst. Preferably, the catalyst contains 0.1 to 5 weight percent of these additional promoter metals.

The weight ratio of these additional promoter elements to the ruthenium, iridium, rhodium and/or platinum promoters is about 1:5-100. Preferably, this ratio is about 1:10.

A solid diluent may be mixed with the active catalytic ingredients. Such diluents may conveniently be low surface area materials, i.e. materials having a surface area of less than 10 $m^2/gm$., such as $TiO_2$, $SnO_2$, $ZnO$, $ZrO_2$, amorphous silicas, aluminas, Alundum, SiC and/or graphite. These diluents may be added in amounts of 5-60 weight percent based on the weight of the diluent with the weight of the active catalytic ingredients plus the weight of the diluent being taken as 100 percent. Techniques for diluting catalysts are shown in U.S. Pat. No. 4,075,231 and U.S. Pat. No. 4,076,731, both of which are incorporated herein by reference. Preferably, the solid diluent material is selected from the group consisting of $TiO_2$ and $ZrO_2$.

In order to deposit the promoter metal on the rare earth exchanged Y-type zeolite support of the present invention, any convenient technique can be employed. For example, the promoter metal in the form of a decomposable salt or other compound can be dissolved in a solvent therefor and the solution so obtained used to impregnate the rare earth exchanged Y-type zeolite material. Chloride salts (i.e. $RuCl_3.3H_2O$, $IrCl_3.4H_2O$, $RhCl_3.3H_2O$ and $PdCl_2$) and acetates (i.e. $Cu(C_2$-

H$_3$O$_2$)$_2$.H$_2$O, Ag(C$_2$H$_3$O$_2$)) dissolved in ethanol or isopropanol as a solvent have been found especially suitable for this purpose. Any other compound (e.g. nitrates, etc.) which yield catalytically active promoters when heated in the presence of oxygen under the calcining conditions discussed below can be employed in place of the chloride salts or acetates. Processes for depositing metals on Y-type zeolite supports are well known as taught in U.S. Pat. No. 3,784,617. This patent further teaches that it is well known to deposit other types of Group VIII metals on rare earth exchanged Y-type zeolites. Therefore, those skilled in the art should have no difficulty in producing catalysts including promoted rare earth exchanged Y-type zeolites as used in the present invention.

Once the promoter metal in chloride or other decomposable compound form is deposited on the rare earth-exchanged Y-type zeolite, the composite so formed is activated by calcination. In accordance with the present invention, calcination is accomplished in a molecular oxygen-containing atmosphere at a temperature of about 250° to 600° C., preferably 350 to 500° C., most preferably 427° C. Temperatures below 250° C. can be employed but activation is so slow that such temperatures are impractical. At temperatures above 600° C., the zeolite support will begin to decompose hence reducing the catalytic activity of the catalyst produced. Calcination has the effect of expelling water from the zeolite support, which in turn causes the calcined catalyst obtained to exhibit a superior catalytic activity. Therefore, calcination should be carried out for a time sufficient to drive off water from the zeolite support and hence improve the catalytic activity of the catalyst obtained. Those skilled in the art can determine the optimum calcination time by simple routine experimentation. In this connection, it has been found that at the preferred calcination temperature of 427° C., the calcination time is approximately two hours, whereas at the maximum calcination temperature of 600° C. calcination should last no more than about eight hours while at the minimum calcination temperature of 250° C. calcination should be accomplished for at least about 24 hours.

Once the promoter metal-containing zeolite composite of the present invention has been subjected to calcination, it can be directly used as the catalyst to effect the hydroalkylation reaction, reduction with hydrogen gas being unnecessary.

As indicated above, the products of the inventive process, namely cycloalkylaromatic hydrocarbons, are produced in accordance with the present invention with high per pass conversions and high selectivities. Thus the present invention marks a significant advance over prior art processes since it is possible to produce more end product with a given amount of feed. Moreover, with superior selectivities, recycle requirements are reduced, thereby decreasing energy costs. Also, because hydrogen reduction of the catalyst prior to use is unnecessary, and because the inventive process can be carried out in single stage operation the inventive process is simpler to accomplish than many analogous prior art processes.

The end products of the inventive process, namely cycloalkylaromatic hydrocarbons, have many significant uses. For example, these compounds can be converted to phenol and/or cyclohexanone in the case of benzene and analogous products in the case of benzene analogs, which compounds have known utilities.

Working Examples

In order to more thoroughly illustrate the present invention, the following working examples are presented. In these examples "% ppc" means percent per pass conversion and is defined as $$\% ppc = \frac{\text{moles carbon in reactant converted to product}}{\text{moles carbon in reactant fed}} \times 100$$

EXAMPLE 1

0.193 gram IrCl$_3$ 4H$_2$O was dissolved in 200 cc distilled water to form a green solution. 9.9 grams Linde's SK-500 (<50 mesh powder) was added, and the water was evaporated from the composition so obtained to form a light brown paste which was dried overnight at 110° C. to form an essentially white material. This material was then calcined in air at 427° C. for 2½ hours to produce a grayish-white catalyst containing 1% Ir and 99% SK-500.

5 grams of the catalyst so obtained were charged into a 600 cc PARR autoclave. 156.22 grams (2.0 moles) benzene was also fed into the reactor. The autoclave was then pressurized with hydrogen to a pressure 400 psig. The reaction progressed for approximately 35 minutes over which time the pressure in the reactor decreased from 400 to 180 psig and the reaction temperature increased from an initial value of 22° C. to 185° C. After the 35 minute reaction period, the reaction product was recovered from the reactor and subjected to analysis by gas chromotography. The following results were obtained:

|  | %ppc |
|---|---|
| cyclohexane | 8.36 |
| bicyclohexane | 0.10 |
| cyclohexylbenzene | 43.94 |
| dicyclohexylbenzene | 0.52 |
| unreacted benzene | 47.09 |
| selectivity | 83.00 |

EXAMPLE 2

The procedure of Example 1 was repeated except that catalyst employed was composed of 1% Rh and 99% SK-500. This catalyst was prepared in the same way as the catalyst employed in Example 1 except that 0.256 grams RhCl$_3$.3H$_2$O was employed rather than 0.193 grams IrCl$_3$.4H$_2$O. Also, in Example 2, the reaction time was 1½ hours rather than ½ hour. The following results were obtained:

|  | % ppc |
|---|---|
| cyclohexane | 32.51 |
| bicyclohexane | 1.80 |
| cyclohexylbenzene | 35.78 |
| dicyclohexylbenzene | 0.52 |
| unreacted benzene | 11.40 |
| selectivity | 40.4 |

EXAMPLE 3

Example 2 was repeated except that the catalyst employed contained 1% Pd and 99% SK-500. The catalyst of Example 3 was prepared as the catalyst of Example 1 was prepared except that 0.167 grams PdCl$_2$ was employed. The following results were obtained:

|  | % ppc |
|---|---|
| cyclohexane | 10.74 |
| bicyclohexane | 0.10 |
| cyclohexylbenzene | 50.44 |
| dicyclohexylbenzene | 4.43 |
| unreacted benzene | 33.46 |
| selectivity | 75.80 |

EXAMPLE 4

U.S. Pat. No. 3,784,617 to Suggitt discloses a process for the catalytic hydroalkylation of mononuclear hydrocarbons in which the catalyst may be ruthenium supported on NH$_4$-exchanged Y-zeolite. This Example 4 as well as the following Comparative Examples A, B and C are presented to show the improved results realized in accordance with the present invention when the catalyst is composed of ruthenium supported on rare earth-exchanged Y-zeolite.

1.056 grams RuCl$_3$3H$_2$O was dissolved in 200 cc of isopropanol to form a red-brown solution. 39.6 grams Linde's SK-500 was added to this red-brown solution, and the solvent was then evaporated with constant stirring at low heat. The green paste formed thereby was dried overnight at 110° C. in an oven to produce a gray powder. A portion of this gray powder was calcined at 427° C. for 2 hours in the presence of air to provide the Example 4 catalyst having 1% Ru and 99% SK-500.

Hydroalkylation of benzene was carried out in the same way as in Example 1 except that the reaction pressure was maintained at about 300 psig and the reaction temperature was maintained at about 200° C. Also, a portion of the liquid reaction medium was withdrawn at ½ hour intervals and the composition of each withdrawn portion determined. The following results were obtained:

EXAMPLE 4
Catalyst: 1% Ru & 99% SK-500 Calcined in Air at 427° C. for 2 Hours

| Experiment No. | Time (in hrs.) | % ppc CHXN | BiCHXN | CHB | DiCHB | Unreacted Benzene | Selectivity |
|---|---|---|---|---|---|---|---|
| 4$_1$ | ½ | 0.49 | ~0 | 13.91 | 0.92 | 84.68 | 90.8 |
| 4$_2$ | 1 | 2.75 | ~0 | 31.67 | 2.72 | 62.86 | 85.3 |
| 4$_3$ | 1½ | 5.05 | 0.24 | 46.57 | 7.02 | 41.12 | 79.1 |
| 4$_4$ | after cooling in autoclave | 6.74 | 0.24 | 46.06 | 6.94 | 40.02 | 76.8 |

EXAMPLE 5

0.022 grams of IrCl$_3$.4H$_2$O was dissolved in 200 mls. of isopropanol to form a black solution. 0.2842 grams of RuCl$_3$.3H$_2$O and 11.68 grams of Linde's SK500 (less than 50 mesh powder) were added to this black solution, and the solvent was evaporated from the composition so obtained to form a paste which was dried overnight at 110° C. The dried paste was then calcined in air at 427° C. for 2½ hours to produce a catalyst containing 1% ruthenium, 0.1% iridium, 99% SK500.

5 grams of the catalyst so obtained were charged to a 600 cc PARR autoclave. 156.22 grams (2.0 moles) benzene was also fed into the reactor. The autoclave was then pressurized with hydrogen to a pressure of 300 psig. The reaction progressed for approximately 1 hour over which time the pressure in the reactor was maintained at 300 psig. The reaction temperature was 200° C. After the 1 hour reaction period, the reaction product was recovered from the reactor and subjected to analysis by gas chromatography. The results are shown in Table I.

EXAMPLE 6

The procedure of Example 1 was repeated except that the catalyst employed was composed of 0.9% ruthenium, 0.1% iridium, 0.1% copper, 98.9% SK500. This catalyst was prepared in the same way as the catalyst employed in Example 5 except that 0.0377 Cu(C$_2$H$_3$O$_2$)$_2$.H$_2$O and 11.87 grams rather than 11.68 grams of Linde's SK500 were also added to the isopropanol-ruthenium-iridium solution. Also, in Example 6, the reaction time was 1.25 hours rather than 1 hour. The results are shown in Table I.

EXAMPLE 7

Example 6 was repeated except that the catalyst employed contained 0.9% ruthenium, 0.1% copper, 99% SK500. The catalyst of Example 7 was prepared in the same way as the catalyst in Example 6 except that no iridium was employed. Also, in Example 7, the reaction time was 3 hours. The results are shown in Table I.

EXAMPLE 8

The procedure of Example 5 was repeated except that the catalyst employed was composed of 0.9% Ru, 0.1% Ag, 99% SK500. This catalyst was prepared in the same way the catalyst employed in Example 7 was except that 0.0186 grams of Ag(CH$_3$CO$_2$) was employed rather than 0.0377 grams of Cu(C$_2$H$_3$O$_2$)$_2$.H$_2$O. Also, in Example 8, the reaction time was 4.1 hours. The results are shown in Table I.

EXAMPLE 9

The procedure of Example 5 was repeated except that the catalyst employed was composed of 1% Rh, 1.4% La, 97.6% SK500. The catalyst was prepared in the same way as the catalyst employed in Example 5 except that 0.3158 grams of RuCl$_3$.3H$_2$O, 0.33805 grams of La$_2$(C$_2$O$_4$)$_3$.H$_2$O and 11.71 grams of Linde's SK500 was employed. Also, in Example 9, the reaction time was 0.75 hours. The results are shown in Table I.

EXAMPLE 10

The procedure of Example 5 was repeated except that the catalyst employed was composed of 0.8% Ru, 0.2% Ag, 99% SK500. This catalyst was prepared in the same way as the catalyst employed in Example 5 except that 0.210 grams of RuCl$_3$.3H$_2$O, 0.0309 grams of Ag(C$_2$H$_3$O$_2$) and 9.9 grams of Linde's SK500 was employed. Also, in Example 10, the reaction time was 2.5 hours. The results are shown in Table I.

EXAMPLE 11

The procedure of Example 5 was repeated except that the catalyst employed was composed of 0.8% Ru, 0.2% Cu, 99% SK500. This catalyst was prepared in the same way as the catalyst employed in Example 5 except that 0.210 grams of $RuCl_3.3H_2O$, 0.0628 grams of $Cu(C_2H_3O_2)_2.H_2O$ and 9.9 grams Linde's SK500 was employed. Also, in Example 11, the reaction time was 5.5 hours. The results are shown in Table I.

EXAMPLE 12

The procedure of Example 5 was repeated except that the catalyst employed was composed of 0.8% Ru, 0.2% Au, 99% SK500. This catalyst was prepared in the same way as the catalyst employed in Example 5 except that 0.21 grams of $RuCl_3.3H_2O$, 0.040 grams of $AuCl_4.3H_2O$ and 9.9 grams of Linde's SK500 were employed. Also, in Example 12, the reaction time was 2 hours. The results are shown in Table I.

EXAMPLE 13

The procedure of Example 5 was repeated except that the catalyst employed was composed of 1% Ru, 0.01% $K_2O$, 98.99% SK500. This catalyst was prepared in the same way as the catalyst employed in Example 5 except that 0.421 grams of $RuCl_3.3H_2O$, 0.0019 grams of KOH and 15.838 grams of Linde's SK500 were employed. Also, in Example 13, the reaction time was ½ hour. The results are shown in Table I.

EXAMPLE 14

The procedure of Example 5 was repeated except that the catalyst employed was composed of 1% Ru, 50% SK500, 49% $TiO_2$. This catalyst was prepared by dissolving 0.263 grams of $RuCl_3.3H_2O$ in 200 cc of isopropanol to obtain a deep red solution. One-half hour later 4.9 grams of high surface area (60 $m^2/gm.$) $TiO_2$ and 5 grams of Linde's SK500 were added to the deep red solution. The solvent was evaporated off to obtain a paste. This paste was dried overnight at about 110° C. to yield a gray-blue material. This gray-blue material was calcined in a furnace for 2 hours at 427° C. Also, in Example 14, the reaction time was 1.33 hours. The results are shown in Table I.

EXAMPLE 15

The procedure of Example 5 was repeated except that the catalyst employed was composed of 0.5% Ru, 0.25% Re, 0.25% Ir, 99% SK500. This catalyst was prepared in the same way as the catalyst employed in Example 5 except that 0.105 grams of $RuCl_3.3H_2O$, 0.036 grams of $NH_4ReO_4$, 0.48 grams of $IrCl_3.4H_2O$ and 9.9 grams of Linde's SK500 was employed. Also, in Example 15, the reaction time was 1 hour. The results are shown in Table I.

TABLE I

| Example Number | Time (In Hours) | Percent PPC | | | | | Selectivity | Catalyst |
|---|---|---|---|---|---|---|---|---|
| | | CHXN | BiCHXN | CHB | DiCHB | Unreacted Benzene | | |
| 5 | 1.00 | 20.00 | 0 | 34.10 | 40.4 | 2.40 | 41.4 | 0.1% Ir, 1% Ru, 98.9% SK500 |
| 6 | 1.25 | 6.90 | 0 | 46.10 | 21.5 | 24.60 | 61.1 | 0.1% Ir, 0.1% Cu, 0.8% Ru, 99% SK500 |
| 7 | 3.00 | 10.80 | 0 | 45.10 | 20.7 | 21.60 | 57.5 | 0.1% Cu, 0.9% Ru, 99% SK500 |
| 8 | 4.10 | 11.00 | 0 | 42.80 | 18.8 | 23.80 | 56.2 | 0.1% Ag, 0.9% Ru, 99% SK500 |
| 9 | 0.75 | 9.70 | 0 | 39.20 | 17.3 | 33.00 | 58.5 | 1.4% La, 1% Ru, 97.6% SK500 |
| 10 | 2.50 | 7.81 | 6.11 | 37.88 | 0.74 | 47.76 | 72.1 | 0.2% Ag, 0.8% Ru, 99% SK500 |
| 11 | 5.50 | 6.00 | trace | 25.38 | 0 | 68.62 | 80.9 | 0.2% Cu, 0.8% Ru, 99% SK500 |
| 12 | 2.00 | 5.59 | 0 | 13.81 | 0 | 80.60 | 71.2 | 0.2% Au, 0.8% Ru, 99% SK500 |
| 13 | 0.50 | 2.17 | 0 | 13.22 | trace | 84.60 | 85.9 | 0.01% $K_2O$, 1% Ru, 99% SK500 |
| 14 | 1.33 | 26.90 | 2.30 | 45.00 | 22.40 | 3.50 | 46.6 | 1% Ru, 49% $TiO_2$, 50% SK500 |
| 15 | 1.00 | 9.40 | 0 | 24.90 | 0 | 66.70 | 72.7 | 0.25% Re, 0.25% Ir, 0.5% Ru, 99% SK500 |

Comparative Example A

Example 4 was repeated except that the catalyst employed was composed of 1% Ru and 99% $NH_4$-exchanged Y-zeolite which was calcined at 427° C. for 2 hours. The following results were obtained:

COMPARATIVE EXAMPLE A
Catalyst: 1% Ru & 99% $NH_4$-Exchanged Y-Zeolite Calcined in Air at 427° C. for 2 Hours

| Experiment No. | Time (in hrs.) | % ppc | | | | | Selectivity |
|---|---|---|---|---|---|---|---|
| | | CHXN | BiCHXN | CHB | DiCHB | Unreacted Benzene | |
| $A_1$ | ½ | 1.78 | ~0 | 20.64 | 1.17 | 76.41 | 87.5 |
| $A_2$ | 1 | 4.06 | ~0 | 34.56 | 4.08 | 57.31 | 89.9 |
| $A_3$ | 1½ | 7.88 | 0.25 | 40.64 | 7.46 | 43.77 | 72.3 |
| $A_4$ | after cooling in autoclave | 9.32 | 0.25 | 40.51 | 8.09 | 41.83 | 69.6 |

Comparative Example B

A portion of the gray powder produced during catalyst preparation in Example 4 was prepared for use in accordance with the technique disclosed in U.S. Pat. No. 3,829,517. Namely, the gray powder was calcined at 800° C. for 2 hours in the presence of air and then reduced with $H_2$ at 480° C. at atmospheric pressure for 2 hours. Example 4 was then repeated using this catalyst. The following results were obtained:

COMPARATIVE EXAMPLE B
Catalyst: 1% Ru & 99% SK-500 Calcined in Air at 800° C.
For 2 Hours and Then Reduced in H₂ at 480° C. for 2 Hours

| Experiment No. | Time (in hrs.) | % ppc | | | | Unreacted Benzene | Selectivity |
|---|---|---|---|---|---|---|---|
| | | CHXN | BiCHXN | CHB | DiCHB | | |
| $B_1$ | ½ | 0.56 | ~0 | 11.36 | 0.23 | 87.85 | 93.5 |
| $B_2$ | 1 | 0.99 | trace | 15.64 | 0.63 | 82.74 | 90.6 |
| $B_3$ | 1½ | 1.60 | trace | 20.19 | 1.25 | 76.96 | 87.6 |
| $B_4$ | after cooling in autoclave | 2.78 | trace | 20.97 | 1.63 | 74.61 | 82.6 |

Comparative Example C

Example 4 was repeated except that the catalyst employed was composed of 1% Ru and 99% NH₄-exchanged Y-zeolite, the catalyst having been calcined at 800° C. for 2 hours in the presence of air and thereafter reduced at 480° C. in the presence of H₂ for 2 hours in accordance with the technique taught in U.S. Pat. No. 3,829,517. The following results were obtained:

COMPARATIVE EXAMPLE C
Catalyst: 1% Ru & 99% NH₄-Exchanged Y-Zeolite Calcined
In Air at 800° C. for 2 Hours and Then Reduced in H₂ for 2 Hours at 480° C.

| Experiment No. | Time (in hrs.) | % ppc | | | | Unreacted Benzene | Selectivity |
|---|---|---|---|---|---|---|---|
| | | CHXN | BiCHXN | CHB | DiCHB | | |
| $C_1$ | ½ | 2.60 | ~0 | 26.25 | 1.53 | 69.62 | 86.4 |
| $C_2$ | 1 | 5.11 | 0.27 | 33.79 | 4.46 | 56.38 | 77.5 |
| $C_3$ | 1½ | 7.34 | 0.27 | 38.24 | 8.02 | 46.13 | 71.0 |
| $C_4$ | after cooling in autoclave | 8.16 | 0.24 | 35.29 | 7.09 | 49.21 | 69.5 |

Comparative Example D

U.S. Pat. No. 3,829,517 to Zuech discloses a catalytic hydroalkylation process employing a ruthenium halide-active clay catalyst which has not been heated under calcination conditions prior to use. This Comparative Example D as well as the following Comparative Examples E and F are presented to show the superiority of the inventive process as illustrated in Example 4 with respect to the process shown in U.S. Pat. No. 3,829,517.

0.7895 grams RuCl₃ 3H₂O was dissolved in 200 cc ethanol to produce a dark red-brown solution. 29.7 grams Filtrol Grade-71 powder was suspended in the solution and impregnated at low heat with constant stirring. The solvent was then removed and the wet powder obtained dried in an oven at 110° C. for 3 hours to produce a gray powder. A portion of the gray powder was calcined at 427° C. in the presence of air for 2 hours in the manner of Example 4 to yield a catalyst containing 1% Ru and 99% Filtrol Grade-71, which was employed as the catalyst in Comparative Example D.

Example 4 was repeated using as the catalyst the catalyst obtained above. The following results were obtained:

COMPARATIVE EXAMPLE D
Catalyst: 1% Ru & 99% Filtrol Grade-71 Calcined in Air for 2 Hours at 427° C.

| Experiment No. | Time (in hrs.) | % ppc | | | | Unreacted Benzene | Selectivity |
|---|---|---|---|---|---|---|---|
| | | CHXN | BiCHXN | CHB | DiCHB | | |
| $D_1$ | ½ | 1.02 | | 8.48 | 0.30 | 90.20 | 86.5 |
| $D_2$ | 1 | 2.40 | trace | 19.73 | 0.73 | 77.14 | 86.3 |
| $D_3$ | 1½ | 4.03 | 0.13 | 25.43 | 1.38 | 69.02 | 82.1 |
| $D_4$ | after cooling in autoclave | 5.23 | 0.12 | 21.49 | 1.51 | 71.66 | 75.8 |

Comparative Example E

Example 4 was repeated using as the catalyst a portion of the gray powder produced during catalyst preparation in Comparative Example D. It will be noted that this catalyst was composed of 1% Ru and 99% SK-500 and was not calcined prior to use. The following results were obtained:

COMPARATIVE EXAMPLE E
Catalyst: 1% Ru & 99% SK-500 Uncalcined

| Experiment No. | Time (in hrs.) | % ppc | | | | Unreacted Benzene | Selectivity |
|---|---|---|---|---|---|---|---|
| | | CHXN | BiCHXN | CHB | DiCHB | | |
| $E_1$ | ½ | 0.60 | ~0 | 1.72 | | 97.68 | 74.1 |
| $E_2$ | 1 | 1.33 | ~0 | 7.32 | 0.11 | 91.25 | 83.6 |

-continued

COMPARATIVE EXAMPLE E
Catalyst: 1% Ru & 99% SK-500 Uncalcined

| Experiment No. | Time (in hrs.) | % ppc CHXN | BiCHXN | CHB | DiCHB | Unreacted Benzene | Selectivity |
|---|---|---|---|---|---|---|---|
| $E_3$ | 1½ | 3.38 | ~0 | 12.98 | 0.32 | 83.32 | 77.8 |
| $E_4$ | after cooling in autoclave | 5.68 | trace | 12.73 | 0.40 | 81.18 | 67.7 |

Comparative Example F

Comparative Example D was repeated except that the catalyst was not calcined prior to use. It will thus be appreciated that the catalyst employed in this comparative example was composed of 1% Ru and 99% Filtrol Grade-71, the catalyst being uncalcined as taught in U.S. Pat. No. 3,829,517. The following results were obtained:

COMPARATIVE EXAMPLE F
Catalyst: 1% Ru & 99% Filtrol Grade-71 Uncalcined

| Experiment No. | Time (in hrs.) | % ppc CHXN | BiCHXN | CHB | DiCHB | Unreacted Benzene | Selectivity |
|---|---|---|---|---|---|---|---|
| $F_1$ | ½ | 0.26 | 0 | 0.62 | 0 | 99.12 | 70.5 |
| $F_2$ | 1 | 0.21 | 0 | 1.01 | 0 | 98.78 | 82.8 |
| $F_3$ | 1½ | 0.29 | 0 | 1.30 | 0 | 98.42 | 81.8 |
| $F_4$ | after cooling in autoclave | 0.35 | 0 | 1.34 | 0 | 98.31 | 79.3 |

We claim:

1. A process for producing cycloalkyl aromatics by the hydroalkylation of mononuclear aromatic hydrocarbons comprising contacting a mononuclear aromatic hydrocarbon and hydrogen with a catalyst comprising a rare earth exchanged Y-type zeolite support carrying a promoter comprising at least one of ruthenium, iridium, rhodium and palladium, and at least one element selected from the group consisting of uranium, thorium, Group VIIB, and Group IB elements, said catalyst having been calcined in molecular oxygen containing atmosphere at a temperature of about 250° to 600° C. prior to use.

2. The process of claim 1 wherein said catalyst contains at least one element selected from the group consisting of Group IB elements.

3. The process of claim 2 wherein said catalyst contains copper.

4. The process of claim 1 wherein said catalyst contains ruthenium.

5. The process of claim 1 wherein said catalyst contains ruthenium, iridium and copper.

6. The process of claim 1 wherein said catalyst additionally contains at least one element selected from the group consisting of lanthanum, lanthanides and Group IA.

7. The process of claim 1 wherein said catalyst is diluted with a low surface area material having a surface area of less than 10 m²/gm comprising at least one of $SnO_2$, $TiO_2$, $ZnO$, and $ZnO_2$.

8. The process of claim 1 wherein calcination is accomplished for a time sufficient to activate said zeolite support.

9. The process of claim 1 wherein said mononuclear aromatic hydrocarbon is selected from the group consisting of benzene and substituted benzene substituted with 1-4 alkyl groups each independently having 1-4 carbon atoms.

10. The process of claim 9 wherein said mononuclear aromatic compound is benzene.

11. The process of claim 1 wherein said catalyst contains greater than about 0.1 weight percent promoter with the weight of said rare earth exchanged Y-type zeolite plus the weight of said promoter being taken as 100%.

12. The process of claim 11 wherein said catalyst contains 0.2 to 10 weight percent promoter.

13. The process of claim 1 wherein said mononuclear aromatic compound is contacted with said catalyst at a temperature between room temperature and about 400° C.

14. The process of claim 1 wherein said process is carried out in the batch mode, said mononuclear aromatic hydrocarbon and hydrogen contacting said catalyst for a period of about 10 minutes to about 6 hours.

15. The process of claim 14 wherein said mononuclear aromatic hydrocarbon and said hydrogen contact said catalyst for a period of more than ½ to 3 hours.

* * * * *